(12) United States Patent
Briggs et al.

(10) Patent No.: US 10,039,818 B2
(45) Date of Patent: Aug. 7, 2018

(54) ATTENUATED PASTEURELLA MULTOCIDA STRAINS

(71) Applicants: The United States of America, as represented by the Secretary of Agriculture, Washington, DC (US); Biotechnology and Research Development Corporation, Peoria, IL (US)

(72) Inventors: Robert E. Briggs, Boone, IA (US); Fred M. Tatum, Ames, IA (US)

(73) Assignees: The United States of America, as represented by the Secretary of Agriculture, Washington, DC (US); Biotechnology Research and Development Corporation, Peoria, IL (US)

( * ) Notice: Subject to any disclaimer, the term of this patent is extended or adjusted under 35 U.S.C. 154(b) by 0 days.

(21) Appl. No.: 15/147,045

(22) Filed: May 5, 2016

(65) Prior Publication Data

US 2017/0319678 A1    Nov. 9, 2017

(51) Int. Cl.
*A61K 39/102* (2006.01)
*C12N 15/74* (2006.01)
*A61K 39/00* (2006.01)

(52) U.S. Cl.
CPC ............ *A61K 39/102* (2013.01); *C12N 15/74* (2013.01); *A61K 2039/522* (2013.01)

(58) Field of Classification Search
None
See application file for complete search history.

(56) References Cited

U.S. PATENT DOCUMENTS

| 9,757,445 B2 * | 9/2017 | Lawrence | A61K 39/102 |
| 2008/0241192 A1 * | 10/2008 | Kumar | A61K 39/102 424/255.1 |
| 2015/0125487 A1 * | 5/2015 | Lawrence | A61K 39/102 424/201.1 |

* cited by examiner

*Primary Examiner* — Brian Gangle
(74) *Attorney, Agent, or Firm* — David L. Marks; Gail E. Poulos; John D. Fado

(57) ABSTRACT

This disclosure provides attenuated *P. multocida* strains which can be used to prepare vaccine compositions useful for protection against *P. multocida*.

12 Claims, 13 Drawing Sheets

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 1
atgatatttg agaagtcggc gg                                          22

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
tgtaattttc gttcccaagg c                                           21

<210> SEQ ID NO 3
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 3
ttccctagct cacagttagg tgat                                        24

<210> SEQ ID NO 4
<211> LENGTH: 27
```

<212> TYPE: DNA
<213> ORGANISM: Artificial Sequence
<220> FEATURE:
<223> OTHER INFORMATION: Chemically Synthesized

<400> SEQUENCE: 4
gtcacacctt gacttttgaa gaattca          27

<210> SEQ ID NO 5
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 5
tctgcaattt ctttccattc ttttgga          27

<210> SEQ ID NO 6
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 6
aattccaatt gcggttcact ttggca           26

<210> SEQ ID NO 7
<211> LENGTH: 4000
<212> TYPE: DNA
<213> ORGANISM: Pasteurella multocida

<400> SEQUENCE: 7

| | | |
|---|---|---|
| gtaatcccaa cgtaaccaat agaggagaac tcataatgaa atttaaaaaa ctactacttg | 60 |
| catctttatg tttaggtgtt tcagcttctg tatttgcagc agattacgat cttaaattcg | 120 |
| gtatggttgc gggtccaagc tcaaacgaat ataaagcagt agaattcttt gcgaaagaag | 180 |
| tgaaagaaaa atccaatggc aaaattgatg tggctatttt ccctagctca cagttaggtg | 240 |
| atgaccgtgt gatgattaaa caattaaaag acggtgcatt agactttacg ttaggtgaat | 300 |
| cagcacgttt ccaaatttac ttcccagaag cagaagtatt tgcgttgcct tatatgattc | 360 |
| ctaattttga aacctctaaa aaagcgttgc tcgacacaaa atttggtcaa ggtttattga | 420 |
| aaaaaattga taaagagtta aacgtacaag tgttatctgt ggcgtataac ggtacacgtc | 480 |
| aaacaacttc taaccgtgca atcaacagca ttgaagacat gaaagggtta aaattacgtg | 540 |
| tacctaacgc ggcaaccaac cttgcttatg caaatacgt gggtgcagcg ccaacaccaa | 600 |
| tggcattctc tgaagtttac cttgcgcttc aaacaaactc tgtggatggt caagaaaacc | 660 |
| cattaccgac aatccaagca caaaaattct atgaagtaca aaaatactta gcgttaacta | 720 |
| accacatctt aaatgaccaa ctttacttaa tcagtaacga tacgttggca gatttaccag | 780 |
| aagatttaca aaaagtggtt aaagatgcag cagcgaaagc cgctgaatat cacactaaac | 840 |
| tcttcgttga cggtgagaac agcttagttg aattcttcaa agtcaaggt gtgacagtca | 900 |
| cacaaccaga cttaaaacca tttaaagcag cacttacacc atactatgat gaatatctca | 960 |
| agaaaaatgg tgaagtcggt aaaatggcga ttgaagaaat ttctaatctc gctaaataaa | 1020 |
| tatagtaacc ttatccctgc gccttaaggg ataaggttcc tttttattgg ttgtcttga | 1080 |
| ggtatctatg aaaataataa ataaattaga agagtggatt ggcggtgtgc tattcattgg | 1140 |

```
aattttctta attctgttag cacaaatcat tgctcgtcaa gtgtttcagt caccgtttat   1200
ttggagtgaa gaactcgcaa gattgctatt tatctatgtc gggctacttg gtatcagcat   1260
gggtatccgt agtcagcagc atgtttatat tgattttta actaacttta tgcccgagaa    1320
agtgagaaag gtgacaaact cctttgttca agttctcatc tttatttcca tcattatttt   1380
cattcattta ggctttaaag tttggatcga ctccagtttt aaaatggaag cgttaactgc   1440
tttcgcttca gatttaattg ggcgcgagac gattgtgcct gaaaaatgga tgtatgcggc   1500
attgcctttt atttcttgtt taatgttatt ccgcttttc caagcgcaag ttgaaaatta    1560
tagaaataag ttaagttata ttcctgtcac ggcatttgtg attggtgcgg tcattatttt   1620
tgcgatttta ttgattgagc cagattggta aaagtcctc cgtatttcaa attatgtgaa    1680
atttggtggt gatgcagtgt atatcacatt agtgatttgg cttgtcatta tgtttgtggg   1740
aaccccggta ggttggtcat tatttattgc gacgttgctt tattttgcga tgacgcgttg   1800
gaatattgtt aactcggcat caaccaagct caccgacagt ttaaatagtt tcccattatt   1860
gagtgtgccg ttctttattt taaccggtat tttaatgaat acgggcgaa ttacagaacg    1920 tatttttgat ttcgcacgtg ccttgctcgg tcattaccgt ggtggtatgg gacacgtgaa   1980
tatcggggca agtttaattt tctcaggtat gtctggttct gcacttgccg atgcaggtgg   2040
tttaggccag ttagaaatta aagccatgcg tgatgctggg tatgacgatg acatctgtgg   2100
tgggattacc gctgcttctt gtattatcgg tccattagtt ccaccaagta ttgcgatgat   2160
tatctatggg gttatttcta accaatctat tgcaaaatta tttattgcgg gttttattcc   2220
tggtgtgctc gtaaccattg cgttaatgat catgaactat tatgtggcga aaaacgtgg    2280 ttatccaaga acacctaaag cgacccttga caacgttgt caggcattta aaaaggccat    2340
ttgggcagtg ttaaccccaa ttttgattat cggtggtatt ttctctggtc tctttacacc   2400
aacggaagcc gcggtgattg cagccttcta ttccattatt atcgggatgt tgtttaccg    2460 agagttgaat ttacaaatgt tgttcaaaag ctgtattgaa gcaatggcga ttacaggggt   2520
aacagcatta atggtgatga cggtcacttt cttggtgac atgattgcac gtgagcaagt    2580
ggctatgaaa attgcagaag tctttgttgc agtagccgat tcaccaacga tggtgttagt   2640
catgatcaac ttattgctct gttccttgg tatgtttatt gatgctttag cattgcaatt    2700
cttggtgtta ccaatgttaa ttccaattgc ggttcacttt ggcattgact taattttctt   2760
tggtgtcatg accacattaa atatgatgat tggtattttg actccaccaa tgggaatggc   2820
attatttgtt gtggcacgtg ttggtaatat gccagtgagt acagtcgcaa aagggggtttt   2880 acctttctta gtaccaattt ttgtgacact ggtgttgatt acaattttcc cacaaattat   2940 caccttata ccaaatcttc tgatgccata atggcgtgaa gaaatggcat tcaaagccaa    3000
tcggactcgg ttggctttaa tttaaaaaac ttgccattca gaattatgct atctgaatcg   3060
gtattcattc ttactaacct aattaattga ggtaataaaa tgaaatttac aaaaacagcg   3120
ttatttacgg tattagcagc aacggcattt gccgcacaag caggtcagta tccagattta   3180
ccagaaggca ttaaagccgg tgcaggtgca ttaattggtg ataccgttta tgtggggtta   3240
ggtggtactg gcacaacaaa attctattca ttaaatttga agatccaaa agagtggaaa    3300 gaaattgcag aattccctgg tggtaaacgt aatcagcctg ttgctgcggg tgtgaatggt   3360
aagctttatg tgtttggtgg tttccaagat acagatgtcg cgaaaaatca aattatcaat   3420
gatgcttatg agtataatcc ggcagataat acgtggacaa aattaagcac acgttctcct   3480
cgttcaacat ctgtgggagc gagtgttgca gcagatggcg gtaaaattta cttcgtaggt   3540
```

| | |
|---|---:|
| gggtaaacc acgaaatttg aatggttta ttccaagatg ttaaagctgc aggtggtgat | 3600 |
| aaagagaaag aaaaagcgat ctttgacccg tatttcaatt tacgcgcaca agatttcttc | 3660 |
| ttctcaccag aaatcatcag ttatgagcca gctaacaatg tatggcgtaa cgaaggctac | 3720 |
| ttcccatatt cgggtcgtgc aggcgctgcg gttgcgatta agatggtaa attattagtc | 3780 |
| gtgaatggtg aagtgaaagc aggtttacgc tcgccaggta ctgcgttagg tacgattggt | 3840 |
| aaagatggcg ttacttggaa aaactcggt gatttaccag caccaacagg ctatgacaaa | 3900 |
| caagatggta ttgcaggcgg tatgggtggt tataccaatg gtcattatat cgtgacaggt | 3960 |
| ggtgcgaact ccctggtgc attagcaaac tatgaaaaag | 4000 |

<210> SEQ ID NO 8
<211> LENGTH: 2146
<212> TYPE: DNA
<213> ORGANISM: Artificial Sequence
<220> FEATURE:
<223> OTHER INFORMATION: Chemically Synthesized

<400> SEQUENCE: 8

| | |
|---|---:|
| gtaatcccaa cgtaaccaat agaggagaac tcataatgaa atttaaaaaa ctactacttg | 60 |
| catctttatg tttaggtgtt tcagcttctg tatttgcagc agattacgat cttaaattcg | 120 |
| gtatggttgc gggtccaagc tcaaacgaat ataaagcagt agaattcttt gcgaaagaag | 180 |
| tgaaagaaaa atccaatggc aaaattgatg tggctatttt ccctagctca cagttaggtg | 240 |
| atgaccgtgt gatgattaaa caattaaaag acggtgcatt agactttacg ttaggtgaat | 300 |
| cagcacgttt ccaaatttac ttcccagaag cagaagtatt tgcgttgcct tatatgattc | 360 |
| ctaattttga aacctctaaa aaagcgttgc tcgacacaaa atttggtcaa ggtttattga | 420 |
| aaaaattga taaagagtta acgtacaag tgttatctgt ggcgtataac ggtacacgtc | 480 |
| aaacaacttc taaccgtgca atcaacagca ttgaagacat gaaagggtta aaattacgtg | 540 |
| tacctaacgc ggcaaccaac cttgcttatg caaaatacgt gggtgcagcg ccaacaccaa | 600 |
| tggcattctc tgaagtttac cttgcgcttc aaacaaactc tgtggatggt caagaaaacc | 660 |
| cattaccgac aatccaagca caaaaattct atgaagtaca aaaatactta gcgttaacta | 720 |
| accacatctt aaatgaccaa ctttacttaa tcagtaacga tacgttggca gatttaccag | 780 |
| aagatttaca aaaagtggtt aaagatgcag cagcgaaagc cgctgaatat cacactaaac | 840 |
| tcttcgttga cggtgagaac agcttagttg aattgcggtt cactttggca ttgacttaat | 900 |
| tttctttggt gtcatgacca cattaaatat gatgattggt atttgactc caccaatggg | 960 |
| aatggcatta tttgttgtgg cacgtgttgg taatatgcca gtgagtacag tcgcaaaagg | 1020 |
| ggttttacct ttcttagtac cattttttgt gacactggtg ttgattacaa ttttcccaca | 1080 |
| aattatcacc tttataccaa atcttctgat gccataatgg cgtgaagaaa tggcattcaa | 1140 |
| agccaatcgg actcggttgg ctttaattta aaaaacttgc cattcagaat tatgctatct | 1200 |
| gaatcggtat tcattcttac taacctaatt aattgaggta ataaaatgaa atttacaaaa | 1260 |
| acagcgttat ttacggtatt agcagcaacg gcatttgccg cacaagcagg tcagtatcca | 1320 |
| gatttaccag aaggcattaa agccggtgca ggtgcattaa ttggtgatac cgtttatgtg | 1380 |
| gggttaggtg gtactggcac aacaaaattc tattcattaa atttgaaaga tccaaaagag | 1440 |
| tggaaagaaa ttgcagaatt ccctggtggt aaacgtaatc agcctgttgc tgcgggtgtg | 1500 |
| aatggtaagc tttatgtgtt tggtggtttc caagatacag atgtcgcgaa aaatcaaatt | 1560 |

-continued

```
atcaatgatg cttatgagta taatccggca gataatacgt ggacaaaatt aagcacacgt    1620
tctcctcgtt caacatctgt gggagcgagt gttgcagcag atggcggtaa aatttacttc    1680
gtaggtgggg taaaccacga aatttggaat ggtttattcc aagatgttaa agctgcaggt    1740
ggtgataaag agaaagaaaa agcgatcttt gacccgtatt tcaatttacg cgcacaagat    1800
ttcttcttct caccagaaat catcagttat gagccagcta acaatgtatg gcgtaacgaa    1860
ggctacttcc catattcggg tcgtgcaggc gctgcggttg cgattaaaga tggtaaatta    1920
ttagtcgtga atggtgaagt gaaagcaggt ttacgctcgc caggtactgc gttaggtacg    1980
attggtaaag atggcgttac ttggaaaaaa ctcggtgatt taccagcacc aacaggctat    2040
gacaaacaag atggtattgc aggcggtatg ggtggttata ccaatggtca ttatatcgtg    2100
acaggtggtg cgaacttccc tggtgcatta gcaaactatg aaaaag                  2146
```

<210> SEQ ID NO 9
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 9

Leu Val Glu Leu Arg Phe
1               5

<210> SEQ ID NO 10
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 10
ttagttgaat tgcggttc                                                    18

ATTENUATED PASTEURELLA MULTOCIDA STRAINS

Each reference cited in this disclosure is incorporated herein in its entirety.

This application incorporates by reference the contents of a 9.2 kb text file created on May 5, 2016 and named "sequencelisting.txt," which is the sequence listing for this application.

TECHNICAL FIELD

This disclosure relates generally to attenuated bacteria and their use in vaccines.

BRIEF DESCRIPTION OF THE DRAWINGS

FIG. 1A, PCR amplification and cloning of *P. multocida* hyaD. Forward primer 5'-atgatatttgagaagtcggcgg-3' (SEQ ID NO:1), reverse primer 5'-tgtaattttcgttcccaaggc-3' (SEQ ID NO:2). FIG. 1B, deletion of BglII fragment from hyaD. FIG. 1C, transfer of insert to pBC. FIG. 1D, insertion of kanamycin cassette. FIG. 1E, swapping of vector for temperature-sensitive (ts) ori. FIG. 1F, integration of replacement plasmid into chromosome. FIG. 1G, resolution of replacement plasmid from chromosome.

FIG. 2A, PCR amplification of nanP/nanU fragments and introduction of genetic deletion. 1062nanPU_F 5'-ttccctagctcacagttaggtgat-3' (SEQ ID NO:3), 1062nanPU_delR 5'-gtcacaccttgactttt-gaagaattca-3' (SEQ ID NO:4), 1062nanPU_R 5'-tctg-caatttctttccattcttttgga-3' (SEQ ID NO:5), 1062nanPU_delF 5'-aattccaattgcggttcactttggca-3' (SEQ ID NO:6). FIG. 2B, transfer of insert with deletion into pBC SK- showing the amino acid sequence (SEQ ID NO:9) and DNA sequence (SEQ ID NO:10) of the nanPU junction. FIG. 2C, insertion of kanamycin cassette. FIG. 2D, swapping of vector for temperature-sensitive (ts) ori. FIG. 2E, integration of replacement plasmid into chromosome. FIG. 2F, resolution of replacement plasmid from chromosome.

DETAILED DESCRIPTION

Figure 1A:
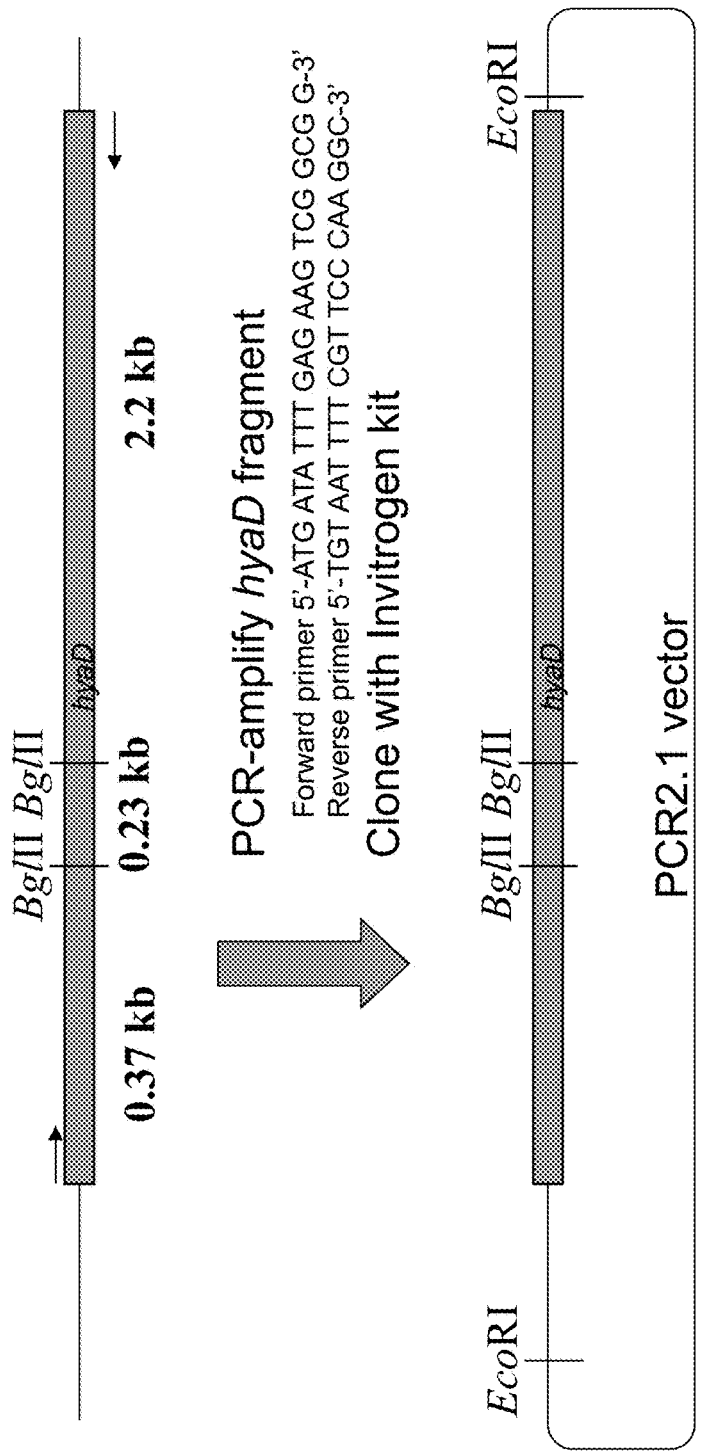
FIGS. 1A-G. Schematics showing stepwise construction of *Pasteurella multocida* (*P. multocida*) P1062 hyaD mutant.
Figure 1B:
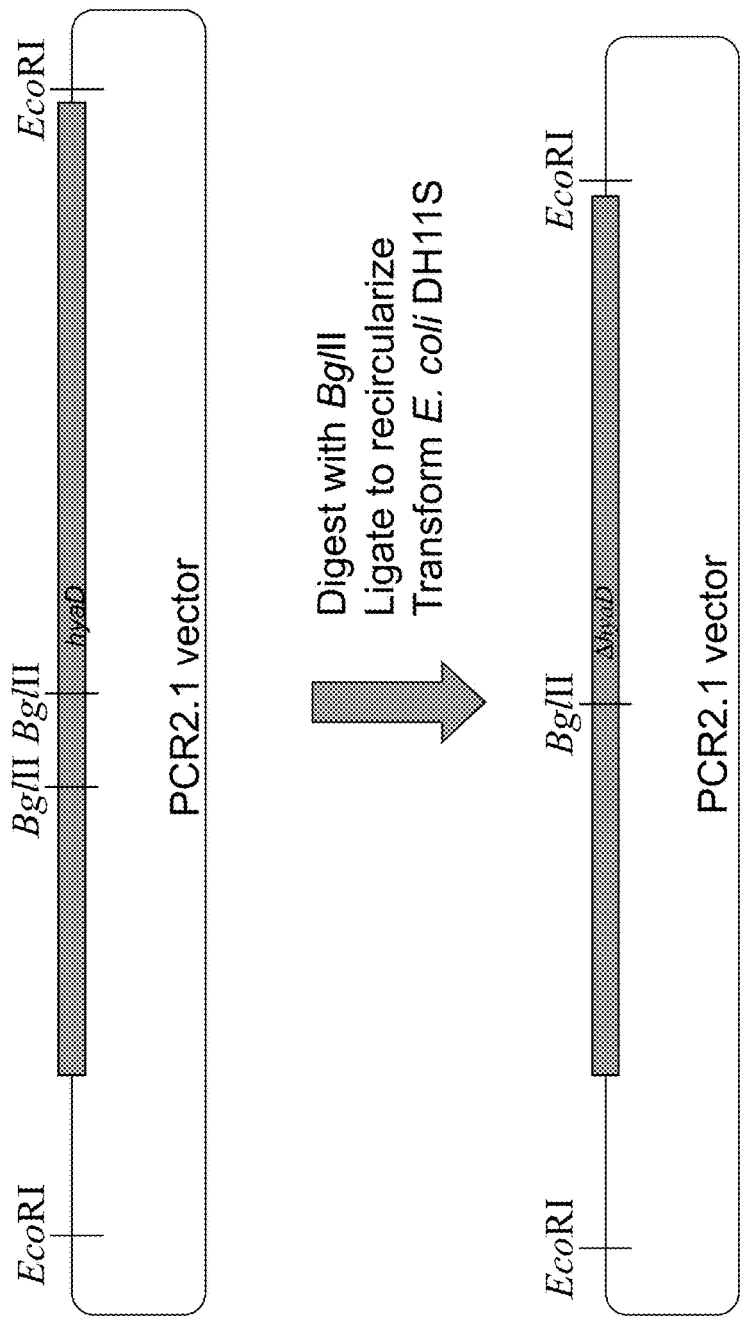
Figure 1C:
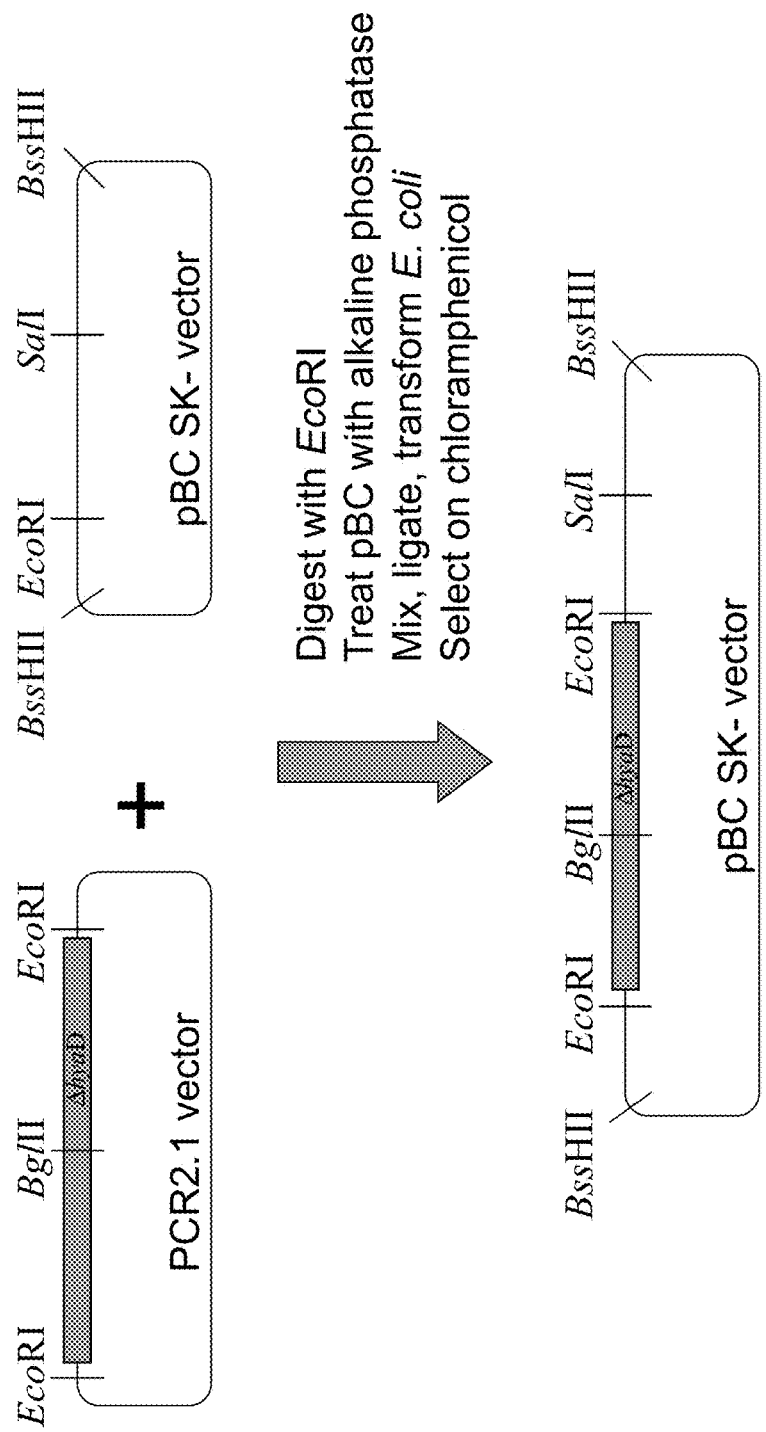
Figure 1D:
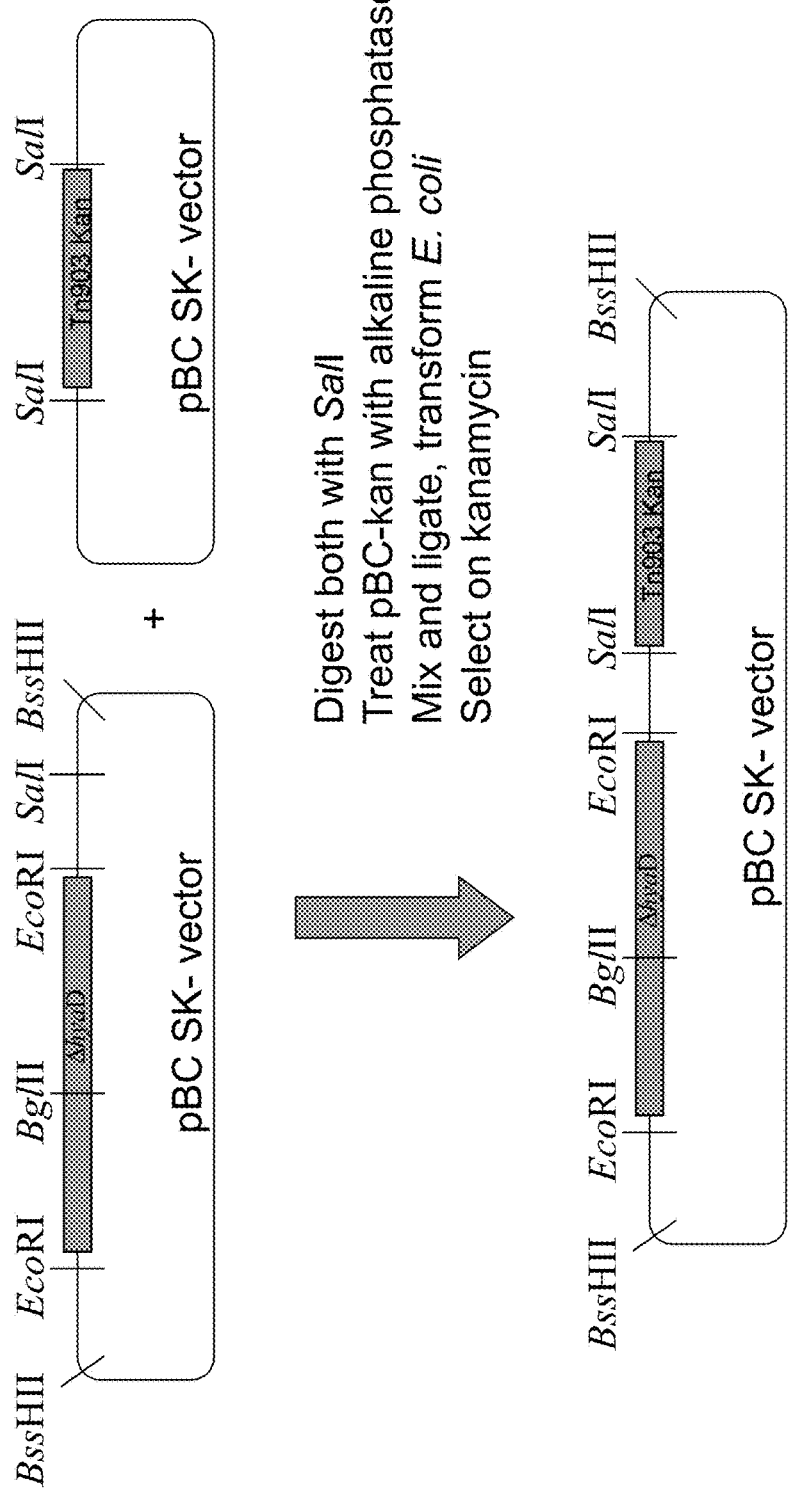
Figure 1E:
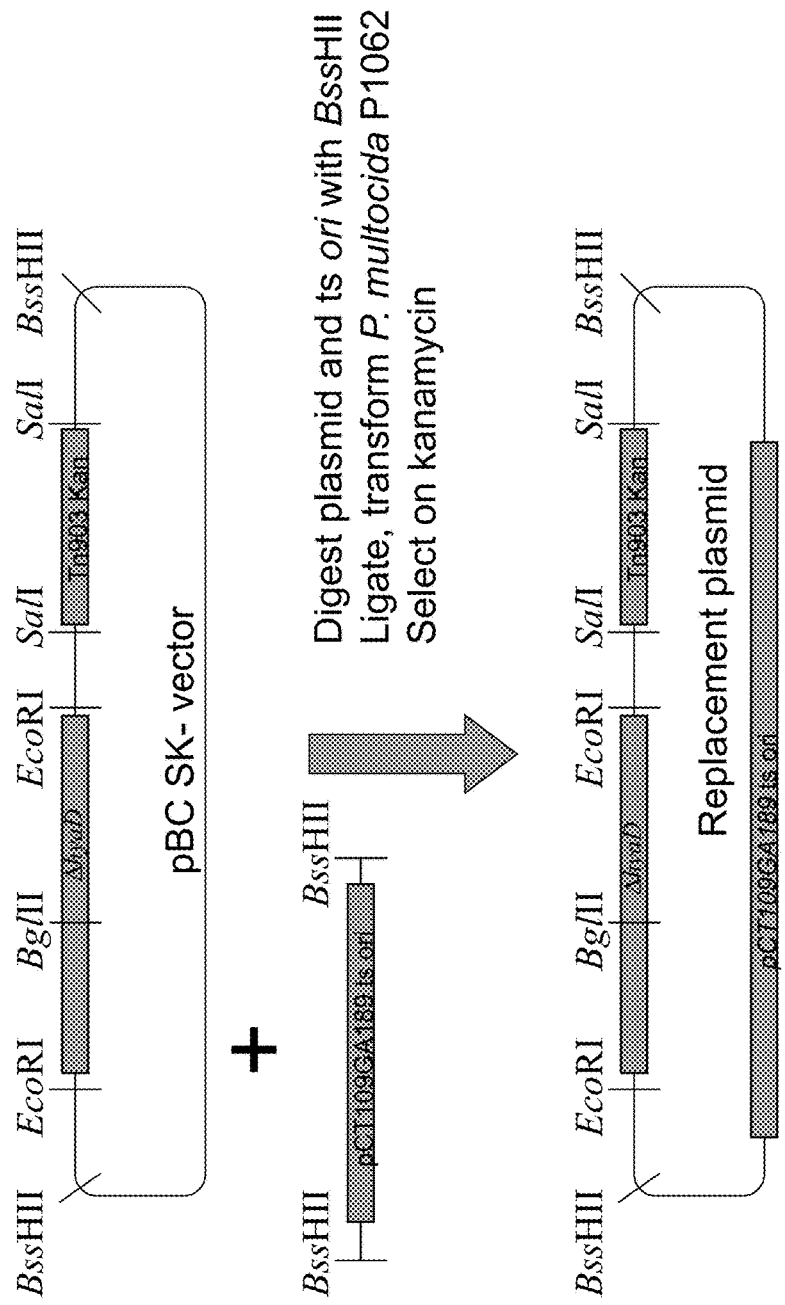
Figure 1F:
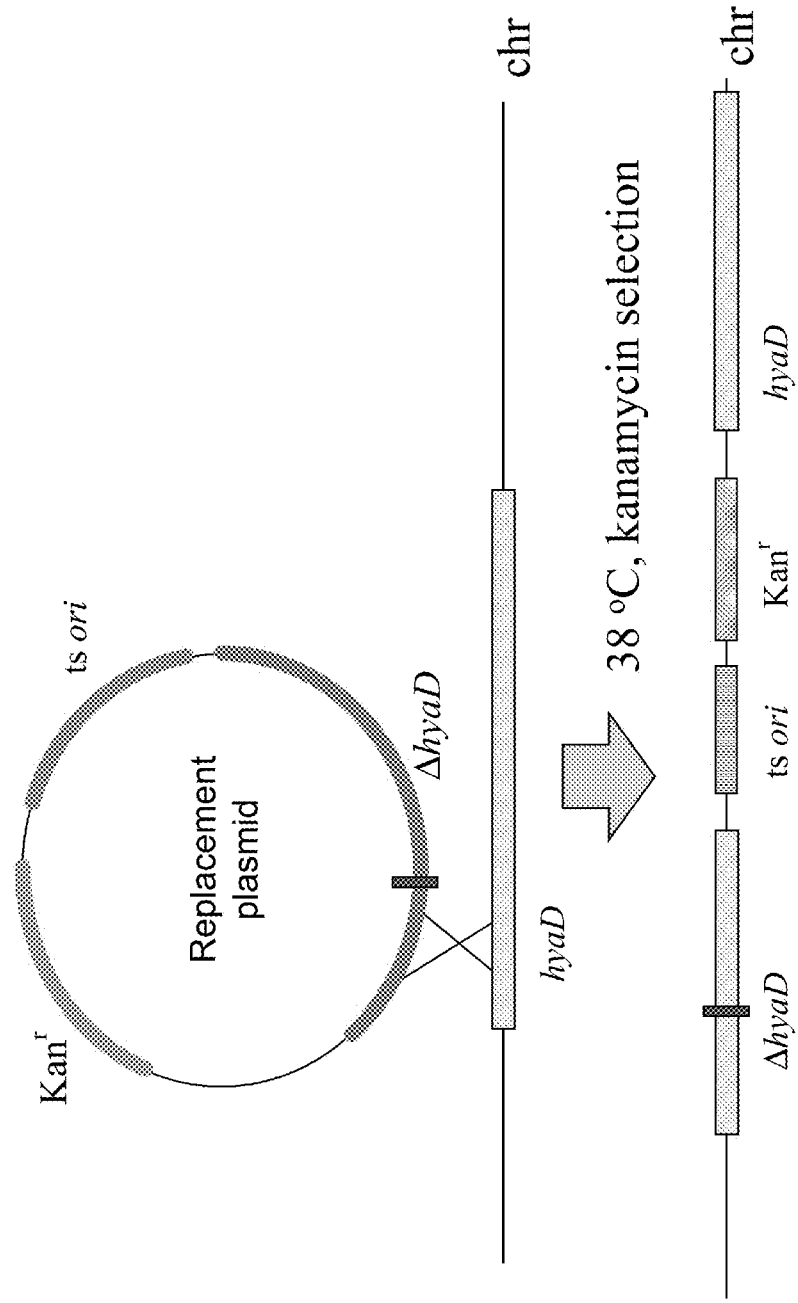
Figure 1G:
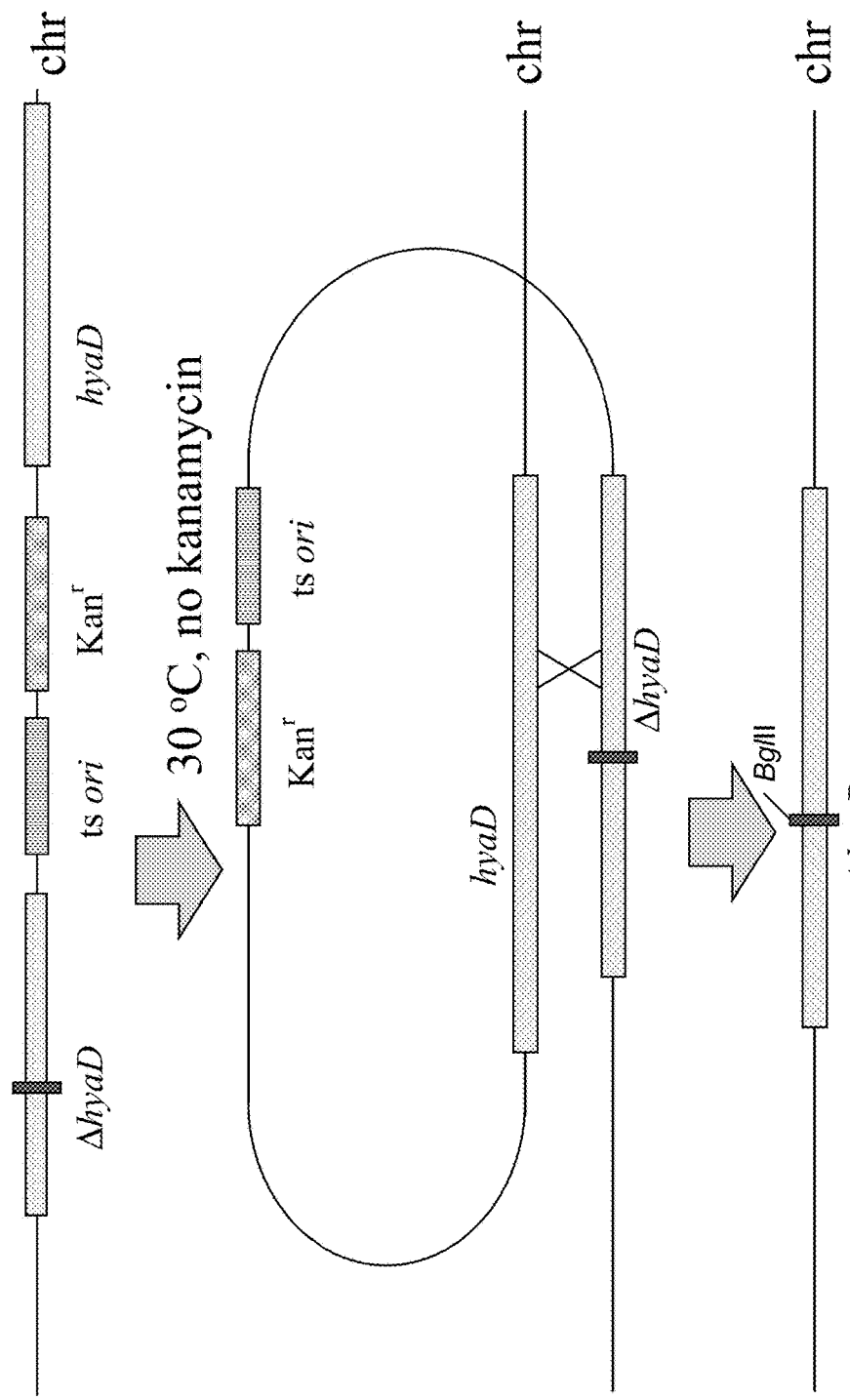
Figure 2A:
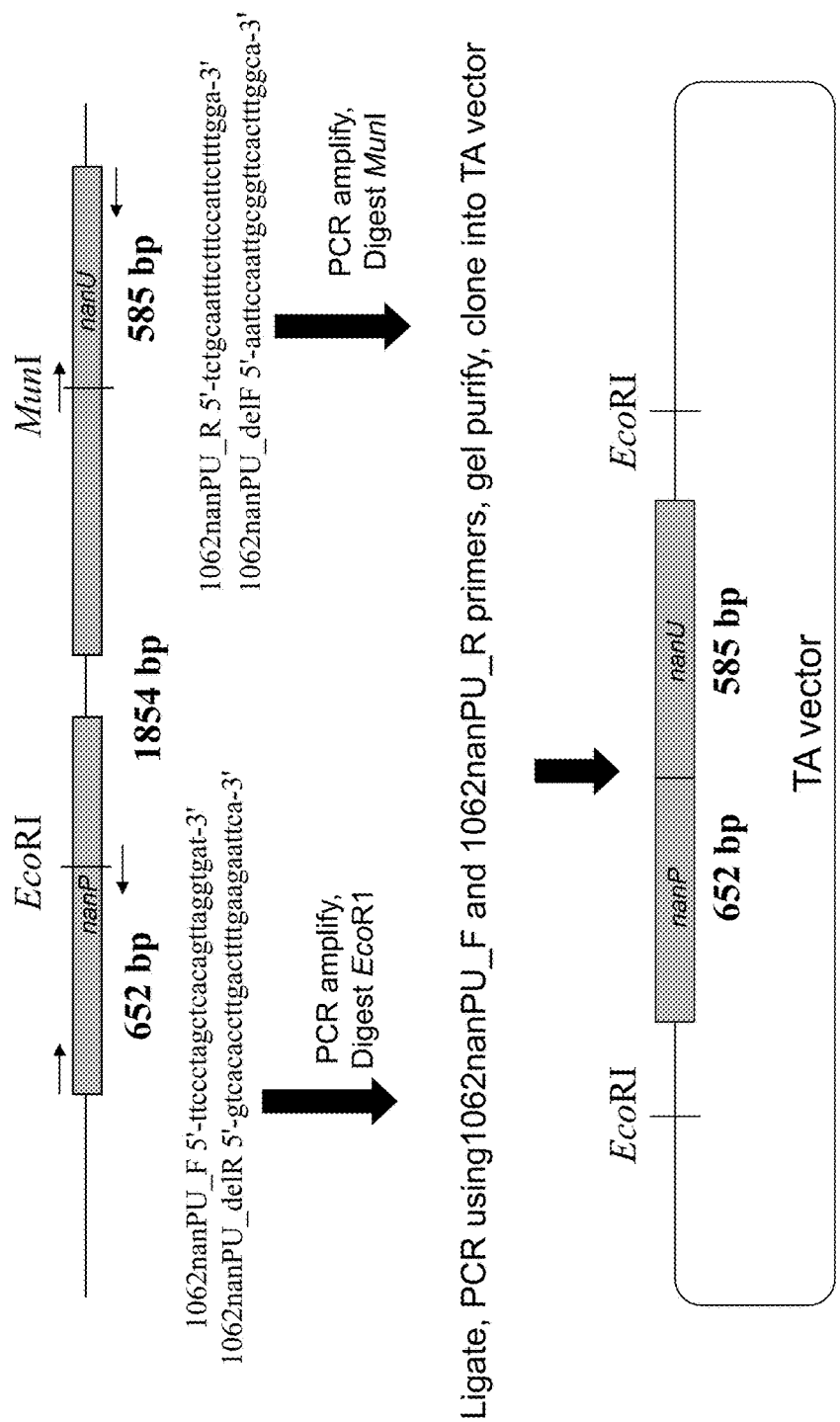
FIGS. 2A-F. Schematics showing stepwise construction of *P. multocida* P1062 nanP/nanU mutant.
Figure 2B:
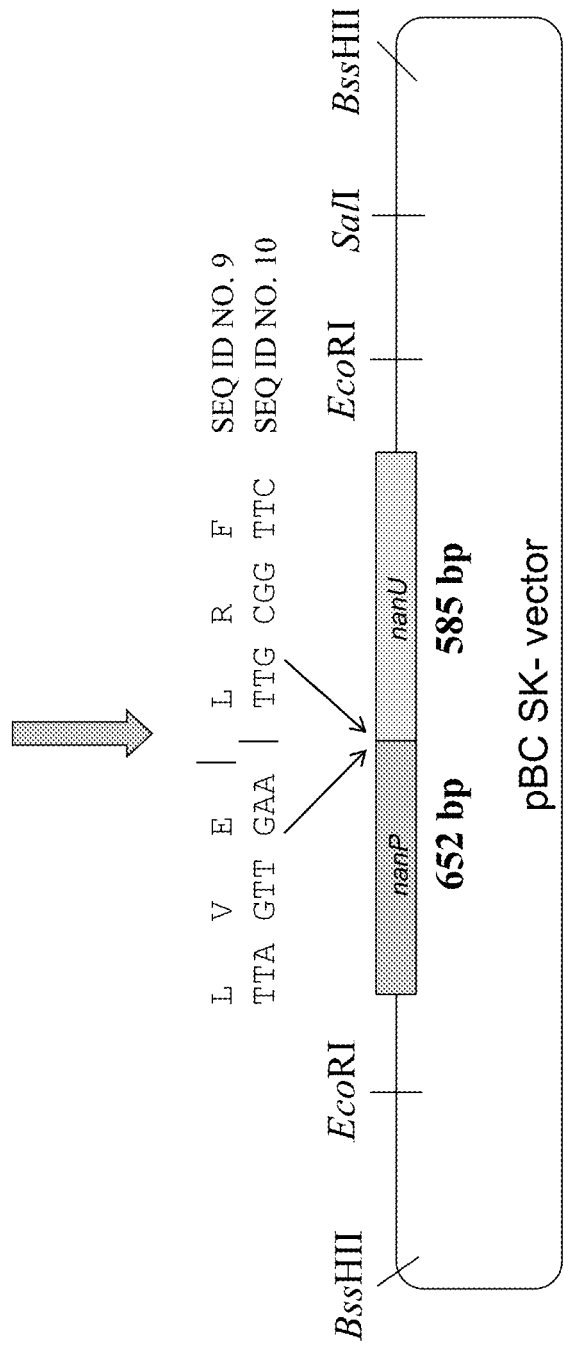
Figure 2C:
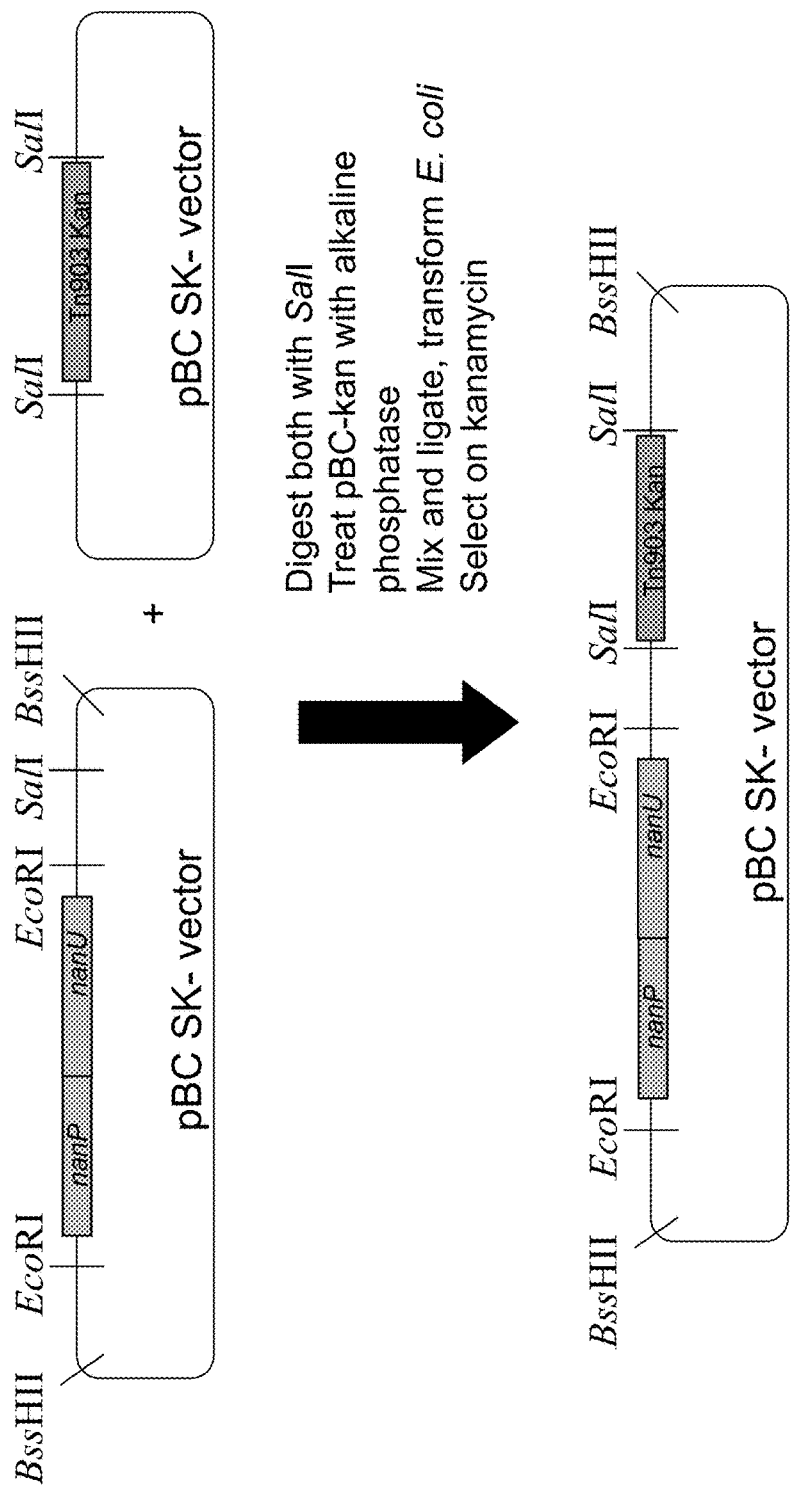
Figure 2D:
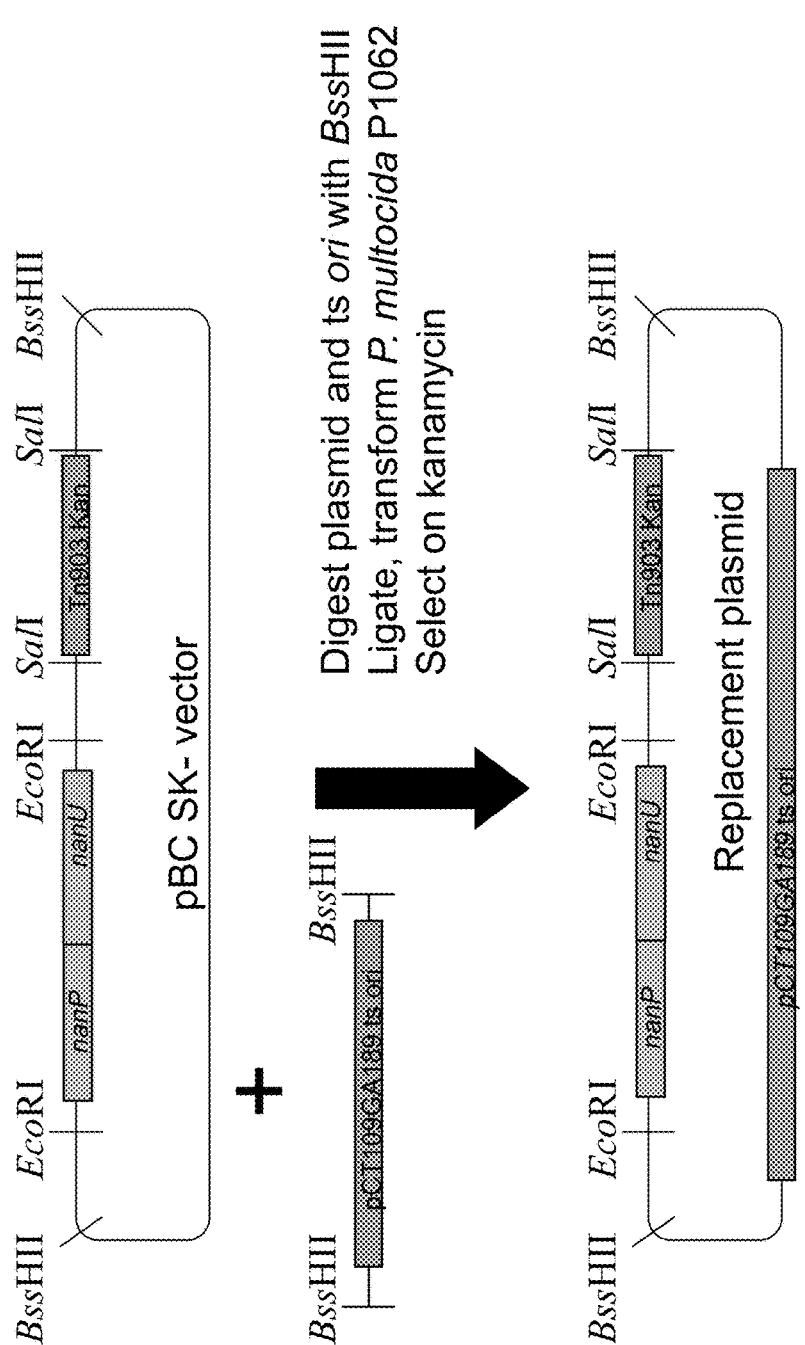
Figure 2E:
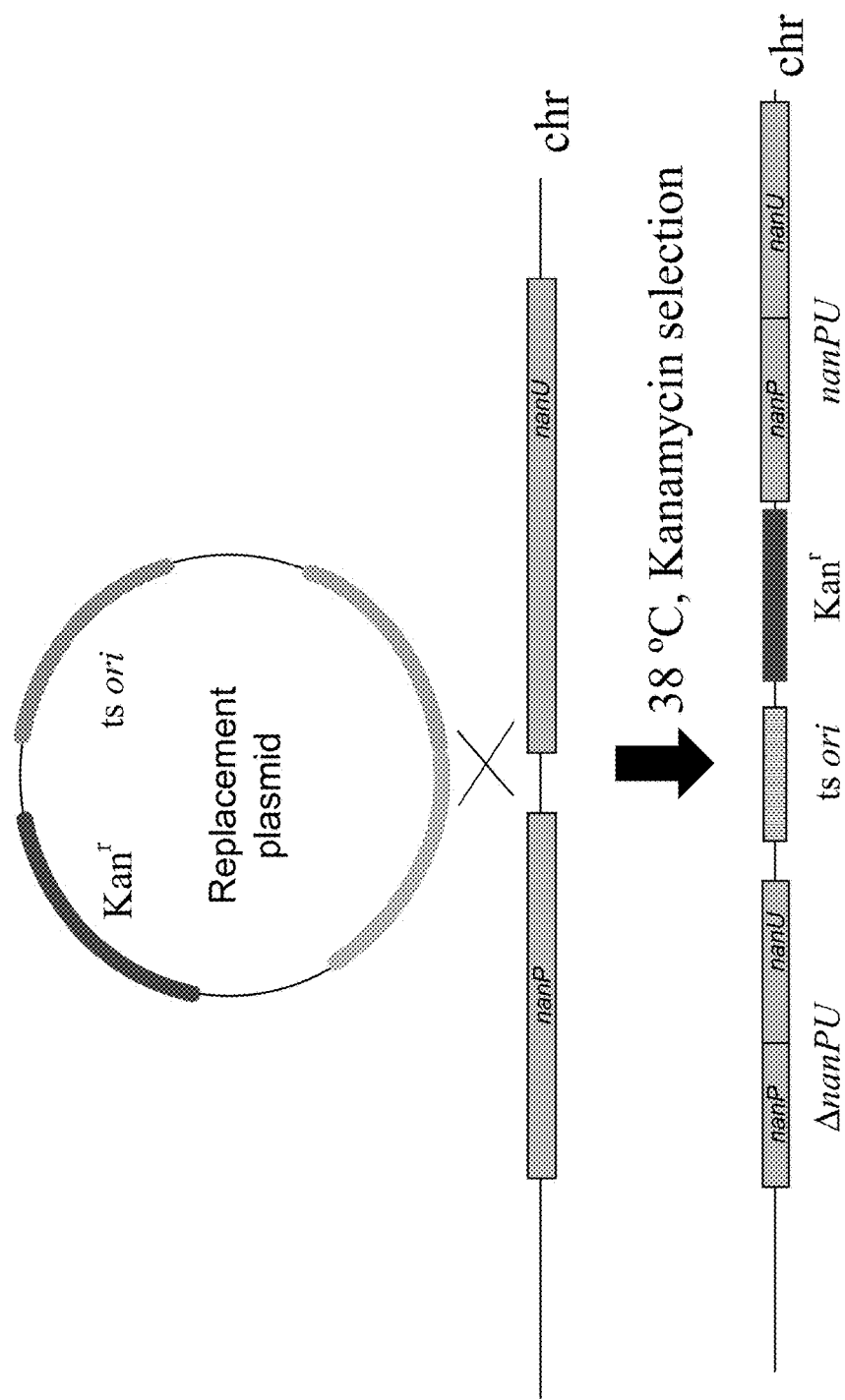
Figure 2F:
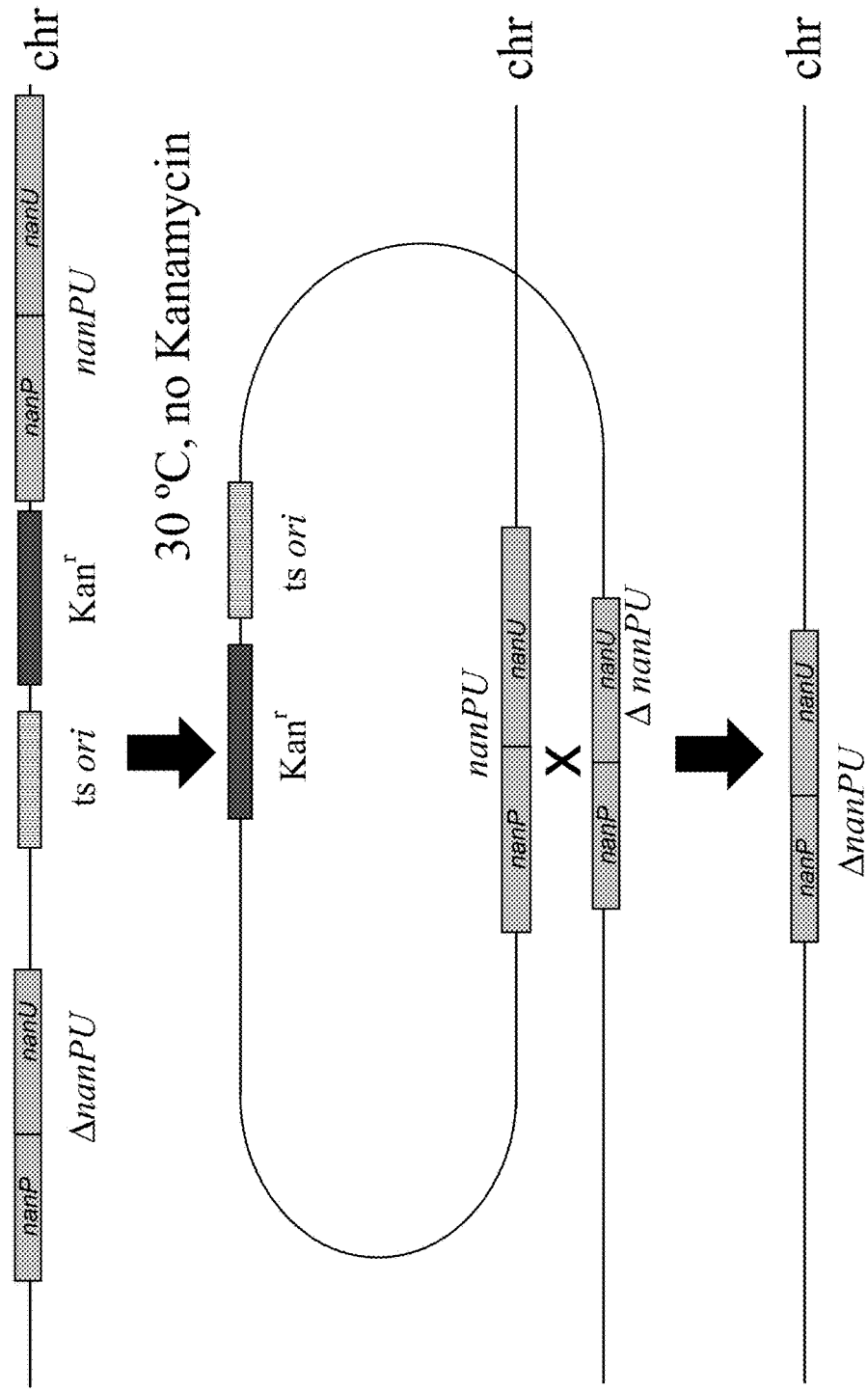

This disclosure provides tools and methods for inducing protective immunity against diseases caused by *P. multocida*, including attenuated *P. multocida* strains which can be used to prepare vaccine compositions useful for protection against *P. multocida*.

In one embodiment, the attenuated *P. multocida* strain contains a deletion in its hyaD gene. This strain is unable to synthesize glycosyl transferase and so exhibits an acapsular phenotype. In another embodiment, the attenuated *P. multocida* strain comprises a deletion bridging its nanP and nanU genes, resulting in a fusion of these genes to form a "nanPU gene," this strain is unable to add sialic acid residues to terminal lipooligosaccharides. In another embodiment, the attenuated *P. multocida* strain contains both the deletion in the hyaD gene and the deletion in the nanP and nanU genes. Genetic engineering of these three attenuated strains is described in the Examples below. All reagents, including the shuttle vectors pCR2.1, pBC SK, and pCT109GA189 is ori, and the *E. coli* DH11S host cell, are known to and accessible by persons skilled in the art.

Vaccine compositions comprise one or more of the attenuated *P. multocida* strains and a pharmaceutically acceptable vehicle and/or carrier. Such carriers are well known to those in the art and include, but are not limited to, large, slowly metabolized macromolecules, such as proteins, polysaccharides, polylactic acids, polyglycolic acids, polymeric amino acids, amino acid copolymers, and inactive virus particles. Pharmaceutically and veterinarily acceptable salts can also be used in the vaccine, for example, mineral salts such as hydrochlorides, hydrobromides, phosphates, or sulfates, as well as the salts of organic acids such as acetates, proprionates, malonates, or benzoates. Vaccines also can contain liquids, such as water, saline, glycerol, and ethanol, as well as substances such as wetting agents, emulsifying agents, or pH buffering agents. Liposomes also can be used as carriers for mutant bacteria. See U.S. Pat. No. 5,422,120, WO 95/13796, WO 91/14445, or EP 524,968 B1.

If desired, an adjuvant can be added to a vaccine. Useful adjuvants include, without limitation, surfactants (e.g., hexadecylamine, octadecylanine, lysolecithin, di-methyldioctadecylammonium bromide, N,N-dioctadecyl-n'-N-bis(2-hydroxyethyl-propane di-amine), methoxyhexadecylglycerol, and pluronic polyols); polyanions (e.g., pyran, dextran sulfate, poly IC, polyacrylicacid, carbopol), peptides (e.g., muramyl dipeptide, dimethylglycine, tuftsin), oil emulsions, alum, and mixtures thereof.

Vaccine compositions comprising one or more of the disclosed attenuated strains can be given alone or as a component of a polyvalent vaccine, i.e., in combination with other vaccines, such as vaccines against *Mannheimia haemolytica* (*M. haemolytica*) and *Histophilus somnus* (*H. somnus*). Mutant bacteria in a vaccine formulation can be live or killed; either live or killed bacteria can be lyophilized and, optionally, reconstituted as is known in the art. Vaccines can conveniently be provided in kits, which also can comprise appropriate labeling and instructions for administering a vaccine to an animal subject (e.g., livestock, an ungulate, a companion animal) or a bird (e.g., poultry).

"Mammals" include monotremes (e.g., platypus), marsupials (e.g., kangaroo), and placentals, which include livestock (domestic animals raised for food, milk, or fiber such as hogs, sheep, cattle, and horses) and companion animals (e.g., dogs, cats). "Ungulates" include, but are not limited to, cattle (bovine animals), water buffalo, bison, sheep, swine, deer, elephants, and yaks. Each of these includes both adult and developing forms (e.g., calves, piglets, lambs, etc.). Any of the disclosed attenuated strains can be administered either to adults or developing mammals, preferably livestock, ungulates, or companion animals.

A convenient method of delivering any of the disclosed attenuated *P. multocida* strains to mammals (such as livestock, ungulates, or companion animals) is by oral administration (e.g., in the feed or drinking water or in bait). It is particularly convenient to top-dress or mix feed with the bacteria. Typically, large animals (e.g., livestock/ungulates such as cattle) are dosed with about $10^6$, $5\times10^6$, $10^7$, $5\times10^7$, $10^8$, $5\times10^8$, $10^9$, $5\times10^9$, or $10^{10}$ cfu; about $10^8$, $5\times10^8$, $10^9$, $5\times10^9$ cfu if feed is top-dressed. Doses of about $10^6$ to about $10^8$, about $2\times10^6$ to about $3\times10^8$, about $2.4\times10^6$ to about $2.6\times10^8$, about $10^4$ to about $10^6$ cfu or of about $10^4$ to about $10^9$ cfu can be given. Doses can be adjusted for smaller livestock/ungulates such as sheep (e.g., about $10^4$, $5\times10^4$, $10^5$, $5\times10^5$, $10^6$, $5\times10^6$, $10^7$, $5\times10^7$, $10^8$, $5\times10^8$ cfu). Analogous dosing regimens can be readily deduced for companion animals.

Other routes for vaccination can also be used. These include without limitation, subcutaneous, intramuscular, intravenous, intradermal, intranasal, intrabronchial, implantation in the ear. Bacteria also can be administered by airspray, by eye inoculation, or by scarification.

"Birds" include wild (e.g., game fowl) and domesticated (e.g., poultry or pet) birds and includes both adult and developing forms (e.g., hatchlings, chicks, poults, etc.). "Poultry" or "poultry birds" include all birds kept, harvested, or domesticated for meat or eggs, including chicken, turkey, ostrich, game hen, squab, guinea fowl, pheasant, quail, duck, goose, and emu.

Any of the disclosed attenuated strains can be administered to a bird by any known or standard technique, including mucosal or intramuscular injection. In a hatchery, bacteria can be administered using techniques such as in ovo vaccination, spray vaccination, or subcutaneous vaccination. On the farm, bacteria can be administered using techniques such as scarification, spray vaccination, eye drop vaccination, in-water vaccination, in-feed vaccination, wing web vaccination, subcutaneous vaccination, and intramuscular vaccination.

Effective doses depend on the size of the bird. Doses range and can vary, for example, from about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $10^9$, to $5\times10^9$ cfu.

US 2015/0125487, incorporated herein by reference, describes vaccination of calves with each of the attenuated strains and subsequent challenge with wild type *P. multocida* 1062. These studies confirmed that each of the three attenuated strains significantly reduced lung lesions compared to control, non-vaccinated calves.

EXAMPLES

Example 1

Generation of Acapsular hyaD Deletion Mutants of *P. multocida* Strain 1062

A *P. multocida* mutant of strain 1062 (bovine, serotype A:3, from pneumonic bovine lung), unable to synthesize capsule, was constructed by deleting a portion of the coding region of hyaD and thereby inactivating the synthesis of glycosyl transferase (Chung et al., FEMS Microbiology Lett. 166, 289-96, 1998). The majority of the coding regions of *P. multocida* 1062 hyaD were obtained by PCR amplification, using the forward primer 5'-atgatatttgagaagtcggcgg-3' (SEQ ID NO:1) and the reverse primer 5'-tgtaattttcgttc-ccaaggc-3' (SEQ ID NO:2). These two primers were synthesized with an oligonucleotide synthesizer (Applied Biosystems Inc., CA) by Integrated DNA Technologies, Inc., Coralville, Iowa. The PCR reactions were carried out using the GeneAmp LX PCR Kit (PE Applied Biosystems, Foster City, Calif.) in a Perkin Elmer GeneAmp 9600 thermocycler. Reaction conditions were 30 cycles, each consisting of 30 seconds at 95° C., 45 seconds at 54° C., and 90 seconds at 72° C.

The PCR-generated hyaD fragment used here extended from the starting methionine codon and ended 85 base pairs upstream of the stop codon. The fragment was inserted into pCR2.1 (Invitrogen Inc., LaJolla, Calif.), and the recombinant plasmid was electroporated into the *E. coli* strain DH11S (Life Technologies, Rockville, Md.), generating the plasmid pCR2.1hyaDPm1062. This plasmid was isolated from *E. coli* by the alkaline SDS method and purified by CsCl centrifugation using standard methods. Both strands of the hyaD gene were sequenced using the Dye Terminator Chemistry kit from PE Applied Biosystems, and samples were run on an ABI Prism 377 DNA Sequencer by the Nucleic Acids Facility, Iowa State University, Ames, Iowa.

The precise deletion within hyaD was produced by treating plasmid pCR2.1hyaDPm1062 with the restriction enzyme BglII. This treatment produced a 225 bp deletion within hyaD, which upon ligation resulted in an in-frame deletion. The deleted hyaD fragment was transferred into the EcoRI site within the multiple cloning site of plasmid pBCSK (Strategene Inc.) to produce pBCSKΔhyaDPm1062. Next, the Tn903 kanamycin resistance element (GenBlock) was inserted into the adjacent SalI site to produce pBCSKΔhyaDPm1062kan$^R$. Construction of the replacement plasmid was completed by ligating BssHII digested pBCSKΔhyaDPm1062kan$^R$ to the 1.2 kb temperature-sensitive origin of replication of plasmid, pCT109GA189 (Briggs and Tatum, Appl. Environ. Microbiol. 71, 7187-95, 2005). Because the ColE1 origin is inactive in *P. multocida*, only the ligation product generating plasmid, pCT109GA189ΔhyaDPm1062kan$^R$, was capable of replicating within *P. multocida* strain 1062.

Replacement plasmid, pCT109GA189ΔhyaDPm1062kan$^R$ was introduced into *P. multocida* strain 1062 as follows. Cells were grown in Columbia broth to a density of $OD_{600}$ of 0.5. The cells were chilled on ice for 10 min and pelleted by centrifugation at 5000×g for 15 min. The cells were resuspended in ice-cold distilled water and pelleted as described above. A second wash was done, and the cell pellet was resuspended 1:3 (bacteria:water) and placed on ice. The competent bacteria (100 μl) were mixed in a 0.1 cm electroporation cuvette (Bio-Rad) with the replacement plasmid ligation mixture. Immediately after adding DNA, the cells were electroporated (Gene pulser, Bio-Rad) at 18,000 V/cm, 800 ohm, and 25 mFd, with resultant time constants ranging from 11 to 15 msec.

Chilled Columbia broth (1 ml) was added to the electroporated cells, and the suspension was incubated at 25° C. for approximately 2 hours. The cells were then plated onto Columbia blood agar plates containing 50 μg/ml kanamycin. Colonies were visible after 24 hour incubation at 30° C. Colonies were transferred to 2 ml of Columbia broth containing 50 μg/ml kanamycin and incubated overnight at 30° C. The next day, approximately 20 μl of the culture was spread onto dextrose starch agar plates containing 50 μg/ml kanamycin and incubated at 38° C., the nonpermissive temperature for the replacement plasmid. Cells possessing integrated replacement plasmid survived antibiotic selection at the non-permissive temperature for plasmid replication. These single-crossover mutants could be easily identified phenotypically because integration of replacement plasmid into hyaD of the host resulted in loss of capsule. Wild-type capsular colonies of *P. multocida* 1062 possess the major capsule component hyaluronic acid, are mucoid in appearance, and, when viewed under obliquely transmitted light exhibit a pearl-like iridescence. In contrast, the acapsular single-crossover mutants are non-mucoid and non-iridescent.

Several single-crossover mutants, possessing integrated replacement plasmid, were transferred to 5 ml Columbia broth without antibiotic supplementation and incubated at 30° C. overnight. The next day, approximately 2 μl of growth was transferred to fresh 5 ml Columbia broth (without antibiotic) and incubated overnight at 30° C. This process was repeated several more times to allow for the resolution of the plasmid and mutant formation. After 5 such passages, cells were transferred to dextrose-starch agar plates without supplemental antibiotic and incubated at 38° C. for 16 hours. The colonies which arose on the non-selection plates consisted of both capsular and acapsular phenotypes. These results were expected; depending on where replacement-plasmid resolution occurred either wild-type or mutant colonies were generated. The initial test to identify double crossover mutants (i.e., acapsular hyaD mutants) involved replica-plating acapsular colonies onto dextrose starch agar plates with and without antibiotic followed by overnight incubation at 38° C. Kanamycin sensitive acapsular colonies were further analyzed by PCR using the hyaD primers described above. The PCR products of the putative hyaD mutants were compared to those of the wild-type parent using agarose gel electrophoresis. PCR products that were of the expected size were sequenced using the hyaD forward (SEQ ID NO:1) and hyaD reverse (SEQ ID NO:2) primers. The putative hyaD mutants also were analyzed by PCR for the absence of temperature sensitive plasmid origin of replication of pCT109GA189 and for the absence of the Tn903 kanamycin resistance element.

Example 2

Generation of nanPU Deletion Mutants of *P. multocida* Strain 1062

Two products were amplified from 1062 genomic DNA using the following primers:

```
                                             (SEQ ID NO: 3)
nanPU_F        5'-ttccctagctcacagttaggtgat-3'

(SEQ ID NO: 4)
nanPU_delR     5'-gtcacaccttgacttttgaagaattca-3'

(SEQ ID NO: 5)
nanPU_ R       5'-tctgcaatttctttccattcttttgga-3'

(SEQ ID NO: 6)
nanPU_delF     5'-aattccaattgcggttcactttggca-3'
```

The two PCR products were digested with EcoR1 and MunI, respectively, then ligated. Amplification of the ligation with nanPU_F and R, resolution on an agarose gel, and recovery of the appropriate size product yielded the desired DNA segment containing an approximately 1850 bp deletion joining the nanP and nanU genes. The product was placed into our replacement vector then introduced into P1062 and passed under appropriate conditions. Colonies were screened for the desired product.

The nucleotide sequence of the wild-type nanP/nanU genes is provided as SEQ ID NO:7. The nucleotide sequence of the mutant nanPU gene is provided as SEQ ID NO:8.

Example 3

Generation of hyaD and nanPU Deletion Mutants of *P. multocida* Strain 1062

A *P. multocida* mutant of strain 1062 (bovine, serotype A:3) containing both a deletion in its hyaD gene and a deletion fusing its nanP and nanU genes was prepared using the methods described in Examples 1 and 2, above.

The invention claimed is:

1. An attenuated *P. multocida* bacterium comprising a deletion in nanP and nanU genes which forms the nanPU gene.

2. The attenuated *P. multocida* bacterium of claim 1, wherein the nanPU gene comprises the nucleotide sequence SEQ ID NO: 8.

3. The attenuated *P. multocida* bacterium of claim 1, wherein said attenuated *P. multocida* bacterium is strain 1062, serotype A:3.

4. The attenuated *P. multocida* bacterium of claim 1, further comprising a deletion within the hyaD gene.

5. A kit comprising (i) an attenuated *P. multocida* bacterium comprising a deletion in nanP and nanU genes which forms the nanPU gene, (ii) a pharmaceutically acceptable carrier, and (iii) instructions.

6. The kit of claim 5, wherein said attenuated *P. multocida* bacterium is strain 1062, serotype A:3.

7. The kit of claim 5, wherein said nanPU gene comprises the nucleotide sequence SEQ ID NO: 8.

8. The kit of claim 5, further comprising an adjuvant.

9. The kit of claim 5, wherein said attenuated *P. multocida* bacterium further comprises a deletion in the hyaD gene.

10. The kit of claim 9, wherein said attenuated *P. multocida* bacterium is strain 1062, serotype A:3.

11. The kit of claim 9, wherein said nanPU gene comprises the nucleotide sequence SEQ ID NO: 8.

12. The kit of claim 9, further comprising an adjuvant.

* * * * *